(12) United States Patent
Shiba et al.

(10) Patent No.: US 9,915,594 B2
(45) Date of Patent: Mar. 13, 2018

(54) SAMPLE ANALYZER AND A SAMPLE ANALYZING METHOD

(71) Applicant: Sysmex Corporation, Kobe-shi, Hyogo (JP)

(72) Inventors: Masaki Shiba, Kobe (JP); Tomoyuki Nishida, Kobe (JP); Yuji Wakamiya, Kobe (JP)

(73) Assignee: Sysmex Corporation, Kobe (JP)

( * ) Notice: Subject to any disclaimer, the term of this patent is extended or adjusted under 35 U.S.C. 154(b) by 450 days.

(21) Appl. No.: 14/810,776

(22) Filed: Jul. 28, 2015

(65) Prior Publication Data

US 2015/0330878 A1 Nov. 19, 2015

Related U.S. Application Data

(62) Division of application No. 13/744,904, filed on Jan. 18, 2013, now Pat. No. 9,151,703.

(30) Foreign Application Priority Data

Jan. 20, 2012 (JP) ................................. 2012-009775

(51) Int. Cl.
*G01N 35/00* (2006.01)
*G01N 1/38* (2006.01)
*G01N 35/02* (2006.01)

(52) U.S. Cl.
CPC ......... *G01N 1/38* (2013.01); *G01N 35/00584* (2013.01); *G01N 35/00594* (2013.01); *G01N 35/00603* (2013.01); *G01N 35/00613* (2013.01); *G01N 35/00693* (2013.01); *G01N 35/00712* (2013.01); *G01N 35/026* (2013.01); *G01N 2001/386* (2013.01)

(58) Field of Classification Search
None
See application file for complete search history.

(56) References Cited

U.S. PATENT DOCUMENTS

| 5,447,838 | A | 9/1995 | Meiklejohn et al. |
| 7,384,604 | B2 | 6/2008 | Eaton et al. |
| 2006/0263836 | A1 | 11/2006 | Connelly et al. |
| 2008/0240988 | A1 | 10/2008 | Wakamiya et al. |
| 2009/0035873 | A1 | 2/2009 | Shibata |
| 2010/0105142 | A1 | 4/2010 | Fukuma et al. |

FOREIGN PATENT DOCUMENTS

JP 2001-228155 A 8/2001

*Primary Examiner* — Erik B Crawford
(74) *Attorney, Agent, or Firm* — Brinks Gilson & Lione

(57) ABSTRACT

Herewith disclosed is a sample analyzer comprising: a measurement section configured to perform a measurement on a sample and generate a measurement value according to the concentration of an analyte in the sample; a memory storing a calibration curve; an analysis section; an output section; and an instruction receiver. When the instruction receiver receives an instruction to perform a diluting measurement on a calibration sample, the measurement section dilutes the calibration sample by a predetermined ratio and performs a measurement on the diluted calibration sample, and the analysis section determines the concentration of the analyte in the diluted calibration sample by applying a measurement value obtained from the diluted calibration sample to the calibration curve. Information generated based on the determined concentration and the known concentration is output.

20 Claims, 11 Drawing Sheets

FIG. 9

Review

Sample No.   Sample type

1234567   Normal

| Item | Time measured | Measurement result | Units | Judgement | Dilution ratio | Correction |
|---|---|---|---|---|---|---|
| HBsAg | 15:37:04 | XXXX.XX | IU/mL | | 1/1 | |
| PIC | 15:37:04 | 9.166 | ug/ml | | 1/40 | ● |
| HBsAb | 15:37:04 | 16.8 | mIU/ml | | 1/1 | |
| | | | | | | |
| | | | | | | |

SAMPLE ANALYZER AND A SAMPLE ANALYZING METHOD

RELATED APPLICATIONS

This application is a divisional patent application of U.S. patent application Ser. No. 13/744,904, filed Jan. 18, 2013, which claims priority under 35 U.S.C. § 119 to JP 2012-009775, filed on Jan. 20, 2012, the entire content of which is hereby incorporated by reference.

FIELD OF THE INVENTION

The present invention relates to a sample analyzer capable of diluting and measuring a sample. The present invention also relates to a sample analyzing method.

BACKGROUND OF THE INVENTION

Sample analyzers such as immunoanalyzers determine the concentration of a component to be measured in a sample by applying a measurement value such as the light absorption to a calibration curve that has been prepared beforehand using a standard sample of known concentration. However, when the concentration of the component in the sample to be measured is too high and exceeds the concentration range covered by the calibration curve, it becomes difficult to accurately determine the concentration of the component to be measured even by applying the measurement value to the calibration curve. In this case, the sample is diluted to obtain a concentration that is within the concentration range covered by the calibration curve, so that the concentration of the component in the sample being measured can be determined by applying the measurement value of the diluted sample to the calibration curve.

Japanese Laid-Open Patent Publication No. 2001-228155 discloses a method of determining antibody or antigen content in serum. According to this method, the concentration of the measurement target component contained in the sample is determined by diluting the sample of unknown concentration by a predetermined factor, applying the measured value of the diluted sample to the calibration curve and converting the measured value to the concentration of the measurement target component in the diluted sample, then multiplying the converted concentration by the dilution ratio in order to obtain the original concentration of the measurement target component contained in the undiluted sample.

Various sources of error are inherent in the diluting measurement of the sample. For example, there is a very small error between the set dilution ratio and the actual dilution ratio when the apparatus dilutes the sample. Dilution may be repeated for a sample of extremely high concentration, and this error may increase according to the repeated dilutions. Furthermore, affinity between a reagent and a diluting solution may produce variance in linearity of dilution. That is, depending on the affinity of the reagent and the diluting solution, the reagent is not necessarily diluted at desired ratio.

SUMMARY OF THE INVENTION

A first aspect of the present invention is a sample analyzer comprising: a measurement section configured to perform a measurement on a sample and generate a measurement value according to the concentration of an analyte in the sample; a memory storing a calibration curve that defines a relationship of a measurement value and a concentration of the analyte; an analysis section; an output section; and an instruction receiver for receiving an instruction to perform a measurement of a sample, wherein, when the instruction receiver receives an instruction to perform a diluting measurement on a calibration sample that contains a known concentration of the analyte, the measurement section dilutes the calibration sample by mixing a diluting fluid and the calibration sample by a predetermined ratio and performs a measurement on the diluted calibration sample; the analysis section determines the concentration of the analyte in the diluted calibration sample by applying a measurement value obtained from the diluted calibration sample to the calibration curve; and the output section outputs information generated based on the determined concentration and the known concentration.

A second aspect of the present invention is a sample analyzer comprising: a measurement section configured to perform a measurement on a sample to quantify an analyte in the sample; and a computer; wherein the computer is programmed to perform (A) a calibration operation, and (B) a sample analysis operation, (A) the calibration operation comprising: (A-1) causing the measurement section to perform a measurement on a plurality of calibration samples, each containing an analyte of known concentration; (A-2) causing the measurement section to dilute a calibration sample containing an analyte of known concentration X at a predetermined ratio with a diluting fluid and to perform a measurement on the diluted calibration sample; (A-3) preparing a calibration curve based on the known concentrations of the calibration samples and the measurement results of (A-1); and (A-4) applying the measurement result of (A-2) to the prepared calibration curve to determine a converted concentration X0, (B) the sample analysis operation comprising: (B-1) causing the measurement section to dilute a sample to be measured at a predetermined ratio with a diluting fluid and to perform a measurement on the diluted sample; (B-2) applying the measurement result of (B-1) to the calibration curve prepared to determine a concentration Y0; and (B-3) using the concentration Y0 and the ratio of the known concentration X and the converted concentration X0 to determine the sample concentration Y.

A third aspect of the present invention is a sample analyzing method comprising the steps of: diluting a calibration sample containing an analyte of known concentration X at a predetermined ratio by mixing with a diluting fluid, and measuring the diluted calibration sample; converting a measurement value of the diluted calibration sample in the computer to a converted concentration X0 by applying the measurement value to a previously prepared calibration curve; diluting a sample to be measured by the predetermined ratio by mixing with a diluting fluid, and measuring the diluted sample; converting a measurement value of the diluted sample to a converted concentration Y0 in the computer by applying the measurement value of the diluted sample to the calibration curve; and determining a concentration Y of the analyte contained in the sample to be measured in the computer by multiplying the concentration Y0 by the ratio of the known concentration X and the converted concentration X0.

BRIEF DESCRIPTION OF THE DRAWINGS

FIG. 9 shows a display example of a display input section;

FIG. 10 shows an example of a calibration curve preparation request screen; and

DETAILED DESCRIPTION OF THE PREFERRED EMBODIMENTS

Figure 1:
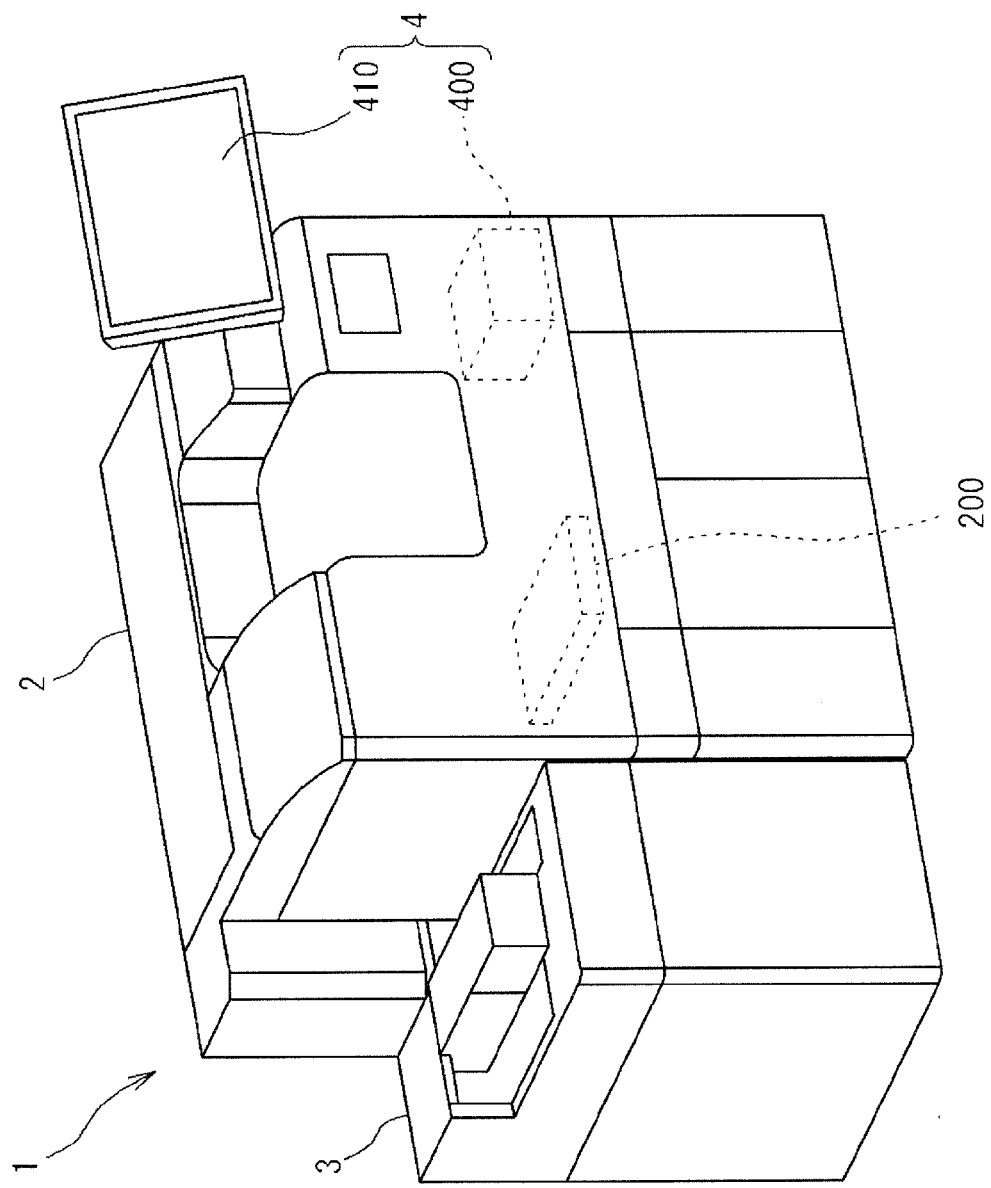
FIG. 1 is a perspective view showing the general structure of an immunoanalyzer as an embodiment of the sample analyzer of the present invention.
Figure 2:
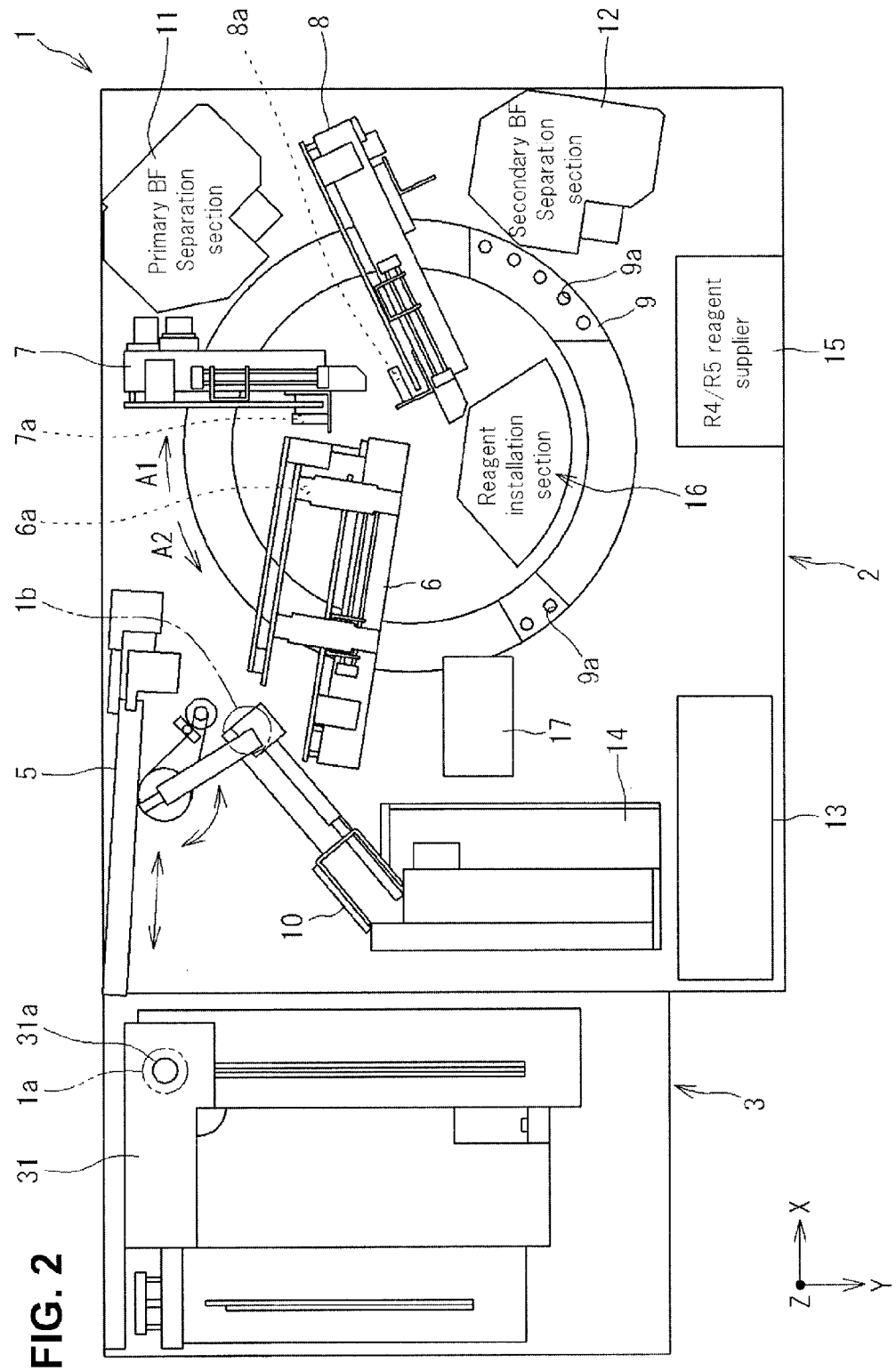
FIG. 2 is a plan view of the immunoanalyzer of FIG. 1.

The embodiments of the sample analyzer of the present invention are described hereinafter with reference to the accompanying drawings. FIG. 1 is a perspective view showing the general structure of the immunoanalyzer 1. FIG. 2 is a plan view of the immunoanalyzer 1 of FIG. 1. The general structure of the immunoanalyzer 1 is first described below.

[General Structure of Immunoanalyzer 1]

The immunoanalyzer 1 examines various items such as hepatitis type-B, hepatitis type-C, tumor marker, and thyroid hormone contained in a serum sample (hereinafter referred to simply as "sample") by utilizing an antigen/antibody reaction. The immunoanalyzer 1 has a measurement section 2, sample transport section (sampler) 3, and a control device 4. The measurement section 2 is communicably connected to the sample transport section 3 and the control device 4 with communication enabled. The sample transport section 3 is configured to transport a rack holding a plurality of test tubes containing sample collected from a subject. The control device 4 has a display input section 410 that includes a touch panel.

As shown in FIG. 2, the measurement section 3 has a sample dispensing arm 5, R1 reagent dispensing arm 6, R2 reagent dispensing arm 7, R3 reagent dispensing arm 8, reactor 9, cuvette supplier 10, primary BF (bound free) separation section 11, secondary BF separation section 12, pipette tip supplier 13, detection section 14, R4/R5 reagent supplier 15, reagent installation section 16, disposal section 17, and controller 200. The sample transport section 3 is configured to transport a rack holding a plurality of test tubes containing unprocessed sample.

At first, the immunoanalyzer 1 mixes the sample to be measured with a buffer solution (R1 reagent). The immunoanalyzer 1 adds a reagent (R2 reagent) containing magnetic particles carrying capture antibody for binding to an antigen contained in the sample to the obtained mixture. The immunoanalyzer 1 attracts the magnetic particles in the mixture by a magnet (not shown in the drawing) of the primary BF (bound free) separation section 11 and removes the component that has not been bound to the capture antibody when magnetic particles are attracted. Then the immunoanalyzer 1 adds a labeling antibody (R3 reagent) to the mixture. The labeling antibody is an antibody carrying an enzymatic marker. After the labeling antibody (R3 reagent) has been added, the immunoanalyzer 1 attracts the magnetic particles in the mixture by a magnet (not shown in the drawing) of the secondary BF (bound free) separation section 12 and removes the R3 reagent containing the unreacted labeling antibody from the mixture when the magnetic particles are attracted. The immunoanalyzer 1 then adds a dispersant (R4 reagent) and a luminescent substrate (R5 reagent), which luminesces by a reaction with the enzymatic marker carried by the labeling antibody to the mixture. The immunoanalyzer 1 then measures the amount of light produced by the reaction between the marker of the labeling antibody and the luminescent substrate. The antigen contained in the sample bound to the labeling antibody can be quantified through this process.

The cuvette supplier 10 is configured to accommodate a plurality of cuvettes, and sequentially supplies the cuvettes one by one to the discharge position 1b where the sample dispensing arm 5 dispenses a quantity of sample.

A pipette 6a for aspirating and dispensing R1 reagent is attached to the R1 reagent dispensing arm 6. The R1 reagent dispensing arm 6 aspirates the R1 reagent in the reagent installation section 16 and dispenses (discharges) the aspirated R1 reagent to a cuvette placed at the discharge position 1b via the pipette 6a.

The pipette tip supplier 13 moves a plurality of loaded pipette tips (not shown in the drawing) one by one to the tip installation position (not shown in the drawing). Thereafter, the pipette tip is mounted on the pipette end of the sample dispensing arm 5 at the tip installation position.

The sample dispensing arm 5 aspirates the sample in the test tube moved to the sample aspirating position 1a by the sample transport section 3 using the installed pipette tip. This aspiration is accomplished through a hole 31a formed in a cover 31 that covers the transport path of the sample transport section 3. The sample dispensing arm 5 dispenses (discharges) the aspirated sample into a cuvette at the discharge position 1b. Prior to discharging the sample to the cuvette, the R1 reagent was previously dispensed to the cuvette by the R1 reagent dispensing arm 6. Thereafter, the cuvette is moved to the reactor 9 by a catcher (not shown in the drawing) of the R1 reagent dispensing arm 6.

A pipette 7a for aspirating and discharging R2 reagent is attached to the R2 reagent dispensing arm 7. The R2 reagent dispensing arm 7 aspirates the R2 reagent in the reagent installation section 16 and dispenses (discharges) the aspirated R2 reagent to a cuvette containing the R1 reagent and the sample.

The reactor 9 has an annular shape so as to circumscribe the reagent installation section 16, which is circular, as shown in the drawing. The reactor 9 has a plurality of cuvette holders 9a arranged at equal spacing along the exterior. Cuvettes set in the cuvette holders 9a are heated to approximately 42 degrees centigrade. Hence, the heating promotes a reaction of the various reagents and the sample in the cuvette. The reactor 9 is configured to be rotatable in a clockwise direction (arrow A1 direction), and moves the cuvette set in the cuvette holder 9a to each processing position where various processes (reagent dispensing and the like) are performed.

The cuvette containing the sample, R1 reagent and R2 reagents is moved by a catcher (not shown in the drawing) from the reactor 9 to the primary BF separation section 11. Primary BF separation is performed in the primary BF separation section 11. The component in the sample that has not bonded to the capture antibody (R2 reagent) is thus removed from the sample within the cuvette. Having completed primary BF separation, the cuvette is returned to the reactor 9 by the catcher (not shown).

A pipette 8a for aspirating and discharging R3 reagent is attached to the R3 reagent dispensing arm 8. The R3 reagent dispensing arm 8 uses the pipette 8a to aspirate the R3 reagent set at the reagent installation section 16. The R3 reagent dispensing arm 8 also uses the pipette 8a to dispense (discharge) the aspirated R3 reagent into the cuvette which was moved from the primary BF separation section 11 to the reactor 9.

The cuvette containing the R3 reagent and the sample is moved from the reactor 9 to the secondary BF separation section 12 by a catcher (not shown in the drawing). Secondary BF separation is performed in the secondary BF separation section 12. The R3 reagent including the unreacted labeled antibody is thereby removed. Having completed secondary BF separation, the cuvette is returned to the reactor 9 by the catcher (not shown).

The R4/R5 reagent supplier 15 sequentially dispenses R4 and R5 reagents to the cuvette.

The reagent installation section 16 holds R1 reagent, R2 reagent, and R3 reagent for each measurement item. The reagent installation section 16 is further provided with a sample diluting fluid (BSA buffer) used to dilute samples when performing diluting measurement of a sample.

The detection section 14 obtains the amount of light produced during the reaction process between the luminescent substrate (R5 reagent) and the labeling antibody (R3 reagent) bonded to the antigen of the ample subjected to predetermined processing with a photomultiplier tube. The detection section 14 transmits the signals corresponding to the amount of light to the controller 200.

The disposal section 17 is a section for the disposal of cuvettes and waste fluid within the cuvettes after detection is completed, and the disposal section has an aspiration part (not shown) for aspirating waste fluid within the cuvette, and a disposal hole (not shown). After detection, the cuvette is moved from the detection section 14 to the disposal section 17 by a catcher (not shown), the waste fluid within the cuvette is aspirated by the aspiration part and the cuvette from which the waste fluid has been aspirated is discarded through the disposal hole in the disposal section 17.

The controller 200 of the measurement section 2 is configured by a CPU, and a memory section such as a ROM, RAM, hard disk, and controls each part of the measurement section 2 according to the signal received from the main body 400 of the control device 4. The controller 200 receives the signals sent from the detection section 14, converts the signals to numerical values, and analyzes the converted measurement values. The controller 200 transmits the analysis results to the main body 400 of the control device 4.

Structure of the Control Device

Figure 3:
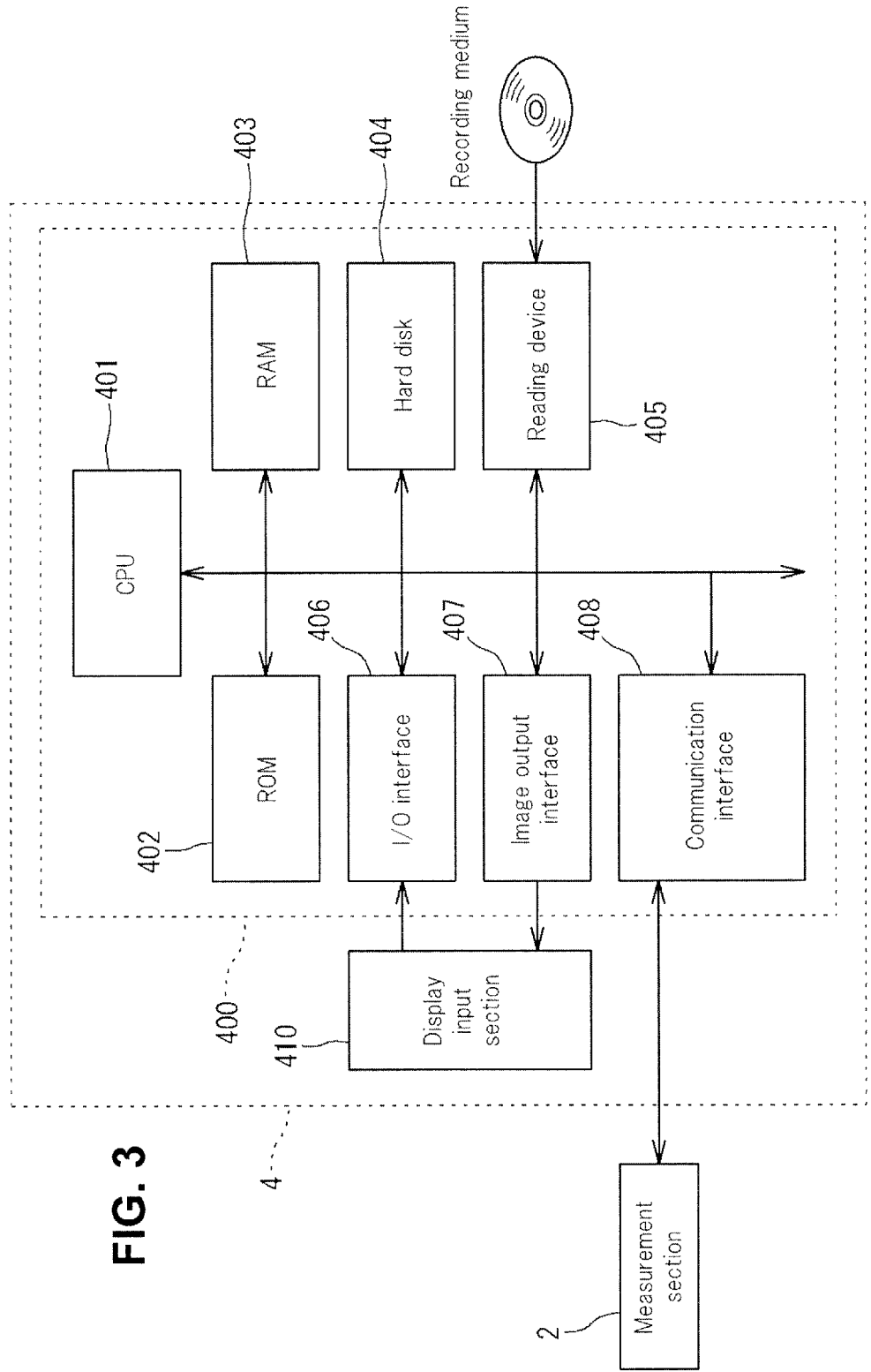
FIG. 3 shows the structure of the control device.

FIG. 3 shows the structure of the control device 4 in the immunoanalyzer 1. The control device 4 is configured by a personal computer that includes a main body 400, and display/input part 410. The main body 400 has a CPU 401, ROM 402, RAM 403, hard disk 404, reading device 405, I/O interface 406, image output interface 407, and communication interface 408.

The CPU 401 is capable of loading a computer program stored in the ROM 402 and executing the computer program in the RAM 403. The RAM 403 is used when reading the computer program stored in the ROM 402 and recorded on the hard disk 404. The RAM 403 is also used as the work area of the CPU 401 when the CPU 401 executes the computer programs.

An operating system and application programs, as well as the data used when executing the operating system and application programs that are executed by the CPU 401, are installed on the hard disk 404.

The reader 405 is a CD drive or DVD drive capable of reading computer programs and data recorded on a recording medium.

The I/O interface 406 receives the signals output from the display/input section 410. The image output interface 407 outputs image signals corresponding to the image data to the display/input section 410. The display/input section 410 displays images based on the image signals received from the image output interface 407, and outputs instructions received from the user through the screen of the display/input section 410 through the I/O interface 406.

Note that a keyboard image is displayed for receiving input text on the display/input section 410 when numerical values are input via the display/input section 410. The user inputs the numerical value by pressing the numbers displayed on the image of the keyboard.

The communication interface 408 transmits signals from the main body 400 to the controller 200 of the control section 2 on the main body 400 side, and receives signals sent from the controller 200 of the control section 2.

[Sample Measurement Flow (without Sample Dilution)]

An embodiment of the method of measuring component in a sample collected from a subject using the previously mentioned immunoanalyzer 1 is described below. The description pertains to measuring a component in an undiluted sample based on the flow chart shown in FIG. 4.

The controller 200 of the measurement section 2 first receives a measurement start signal from the main body 400 of the control device 4, and in step S401 the various drive mechanisms of the sample dispensing arm 5 and the like are placed on standby at the origin position, then the cuvette supplier 10 is actuated to deliver a new cuvette to the discharging position 1b of the sample dispensing arm 5.

In step S402, the controller 200 of the measurement section 2 rotates the R1 reagent dispensing arm 6 until the tip of the pipette 6a of the R1 reagent dispensing arm 6 is positioned above the R1 reagent disposed on the reagent installation section 16, and aspirates a predetermined amount of R1 reagent using the pipette 6a. Thereafter, the R1 reagent dispensing arm 6 is rotated until the tip of the pipette 6a is positioned above the cuvette arranged at the discharging position 1b, and the aspirated R1 reagent is dispensed into the cuvette.

In step S403, the controller 200 of the measurement section 2 aspirates a predetermined amount of sample in the test tube that has been moved to the sample aspirating position 1a by the sample transport section 3 using the pipette tip mounted on the pipette end of the sample dispensing arm 5 at the tip installation position. Thereafter, the sample dispensing arm 5 is rotated until the pipette tip mounted on the pipette end of the sample dispensing arm 5 is positioned above the cuvette disposed at the discharging position 1b, and the aspirated sample is dispensed into the cuvette.

In step S404, the controller 200 of the measurement section 2 actuates a catcher (not shown in the drawing) of the R2 reagent dispensing arm 6 to move the cuvette disposed at the discharging position 1b to a predetermined cuvette holding section 9a of the reactor 9.

In step S405, the controller 200 of the measurement section 2 rotates the R2 reagent dispensing arm 7 until the tip of the pipette 7a of the R2 reagent dispensing arm 7 is positioned above the R2 reagent disposed on the reagent installation section 16, and aspirates a predetermined amount of R2 reagent using the pipette 7a. Thereafter, the R2 reagent dispensing arm 7 is rotated until the tip of the pipette 7a is positioned above the cuvette arranged at the cuvette holding position 9a, and the aspirated R2 reagent is dispensed into the cuvette containing the R1 reagent and sample.

In step S406, the controller 200 of the measurement section 2 actuates a catcher (not shown in the drawing) to move the cuvette containing the sample and R1 and R2 reagents from the cuvette holding position 9a of the reactor 9 to the primary BF separation section 11.

In step S407, the controller 200 of the measurement section 2 performs primary BF separation to remove the component in the sample that is not bonded to the capture antibody from the sample in the cuvette.

In step S408, the controller 200 of the measurement section 2 actuates a catcher (not shown in the drawing) to move the cuvette disposed at the primary BF separation section 11 after primary BF separation has been performed to the cuvette holding position 9a of the reactor 9.

In step S409, the controller 200 of the measurement section 2 rotates the R3 reagent dispensing arm 8 until the tip of the pipette 8a of the R3 reagent dispensing arm 8 is positioned above the R3 reagent disposed on the reagent installation section 16, and aspirates a predetermined amount of R3 reagent using the pipette 8a. Thereafter, the R3 reagent dispensing arm 8 is rotated until the tip of the pipette 8a is moved to a position above the cuvette arranged at the cuvette holding position 9a of the reactor 9, and the aspirated R3 reagent is dispensed into the cuvette.

In step S410, the controller 200 of the measurement section 2 actuates a catcher (not shown in the drawing) to move the cuvette containing the dispensed R3 reagent from the cuvette holding position 9a of the reactor 9 to the secondary BF separation section 12.

In step S411, the controller 200 of the measurement section 2 performs secondary BF separation to remove the R3 reagent containing the unreacted labeling antibody from the cuvette.

In step S412, the controller 200 of the measurement section 2 actuates a catcher (not shown in the drawing) to move the cuvette disposed at the secondary BF separation section 12 after secondary BF separation has been performed to the cuvette holding position 9a of the reactor 9.

In step S413, the controller 200 of the measurement section 2 actuates a catcher (not shown in the drawing) to move the cuvette from the cuvette holding position 9a of the reactor 9 to the R4/R5 reagent supplier 15. Thereafter, the R4/R5 reagent supplier 15 is actuated to dispense R4 reagent into the cuvette.

In step S414, the controller 200 of the measurement section 2 actuates a catcher (not shown in the drawing) to move the cuvette disposed at the R4/R5 reagent supplier 15 to the cuvette holding position 9a of the reactor 9. Thereafter, the R4/R5 reagent supplier 15 is actuated to dispense R5 reagent into the cuvette containing the R4 reagent.

In step S415, the controller 200 of the measurement section 2 actuates a catcher (not shown in the drawing) to move the cuvette containing the dispensed R4 and R5 reagents held at the cuvette holding position 9a of the reactor 9 to the detection section 14. Thereafter, the amount of light produced in the reaction process between the marker of labeling antibody and the luminescent substrate is measured by a photomultiplier tube. The signal corresponding to the measured amount of light is transmitted to the controller 200, converted to a numerical value and stored in memory.

In step S416, the measured cuvette is moved from the detection section 14 to the disposal section 17 by a catcher (not shown in the drawing), and in the disposal section 17 the sample (waste liquid) remaining in the cuvette is aspirated by the aspirating unit, then the empty cuvette is discarded through the disposal hole of the disposal section 17.

[Sample Measurement Flow (With Sample Dilution)]

Figure 5:
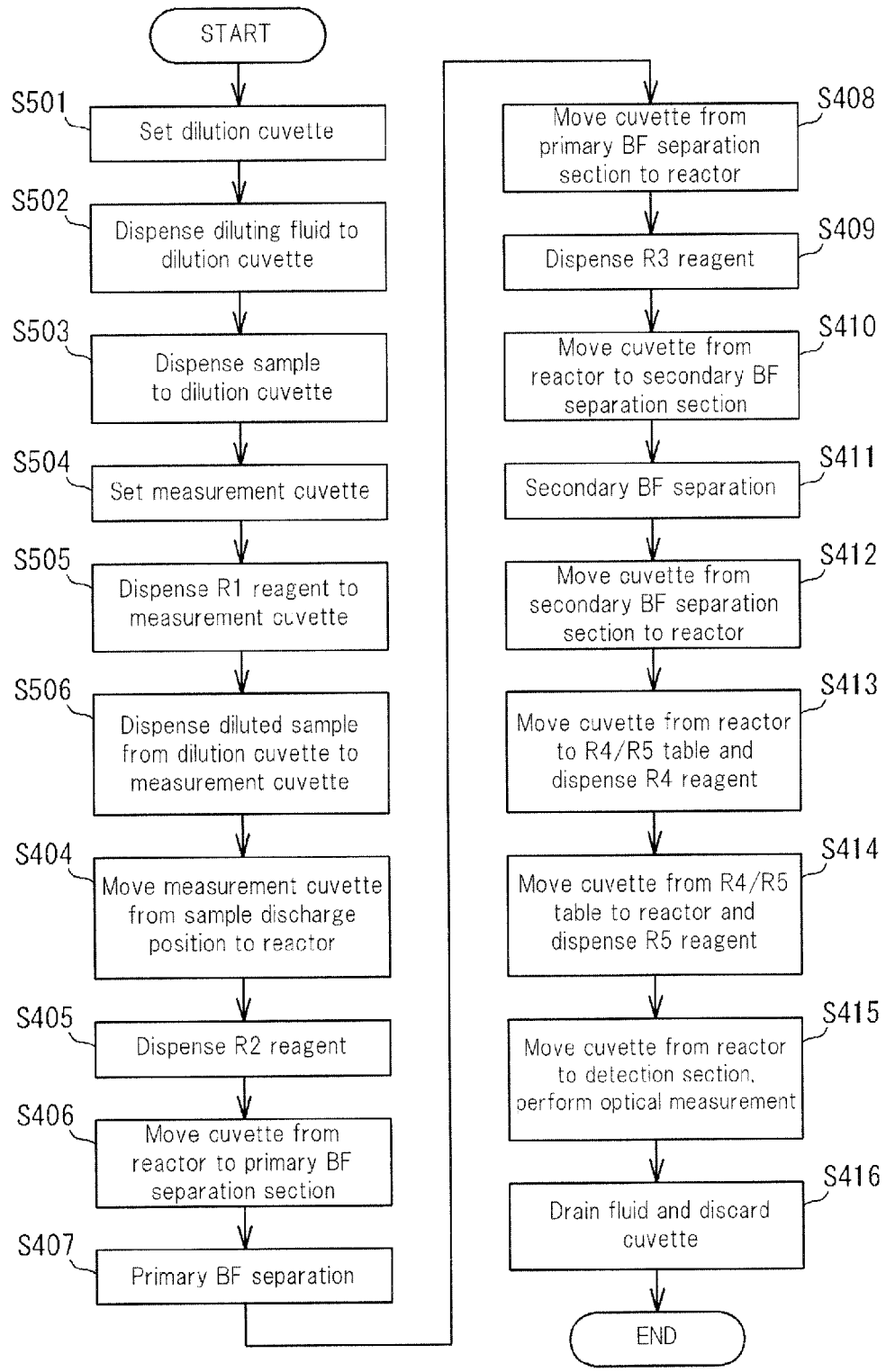
FIG. 5 is a flow chart of the sample measurement when the sample is diluted.

The following description pertains to measuring a component in a sample diluted 40 times based on the flow chart shown in FIG. 5. The immunoanalyzer of the present embodiment measures measurement items such as PIC (plasmin inhibitor complex) tumor marker, CEA (carcinoembryonic antigen), AFP (alpha fetoprotein), infection marker HBsAg (hepatitis type B antigen examination), HBsAb (hepatitis type B antibody examination) and the like. These measurement items, and especially for tumor marker, the concentration of the component to be measured is very high in the sample of a positive patient, and the measured values may exceed the range covered by the calibration curve (over range). In such cases, the analyte is diluted prior to measurement to ensure the measured value of the analyte is within the range covered by the calibration curve. The flow of the series of diluting and measuring the analyte is described below based on the flow shown in FIG. 5.

Figure 4:
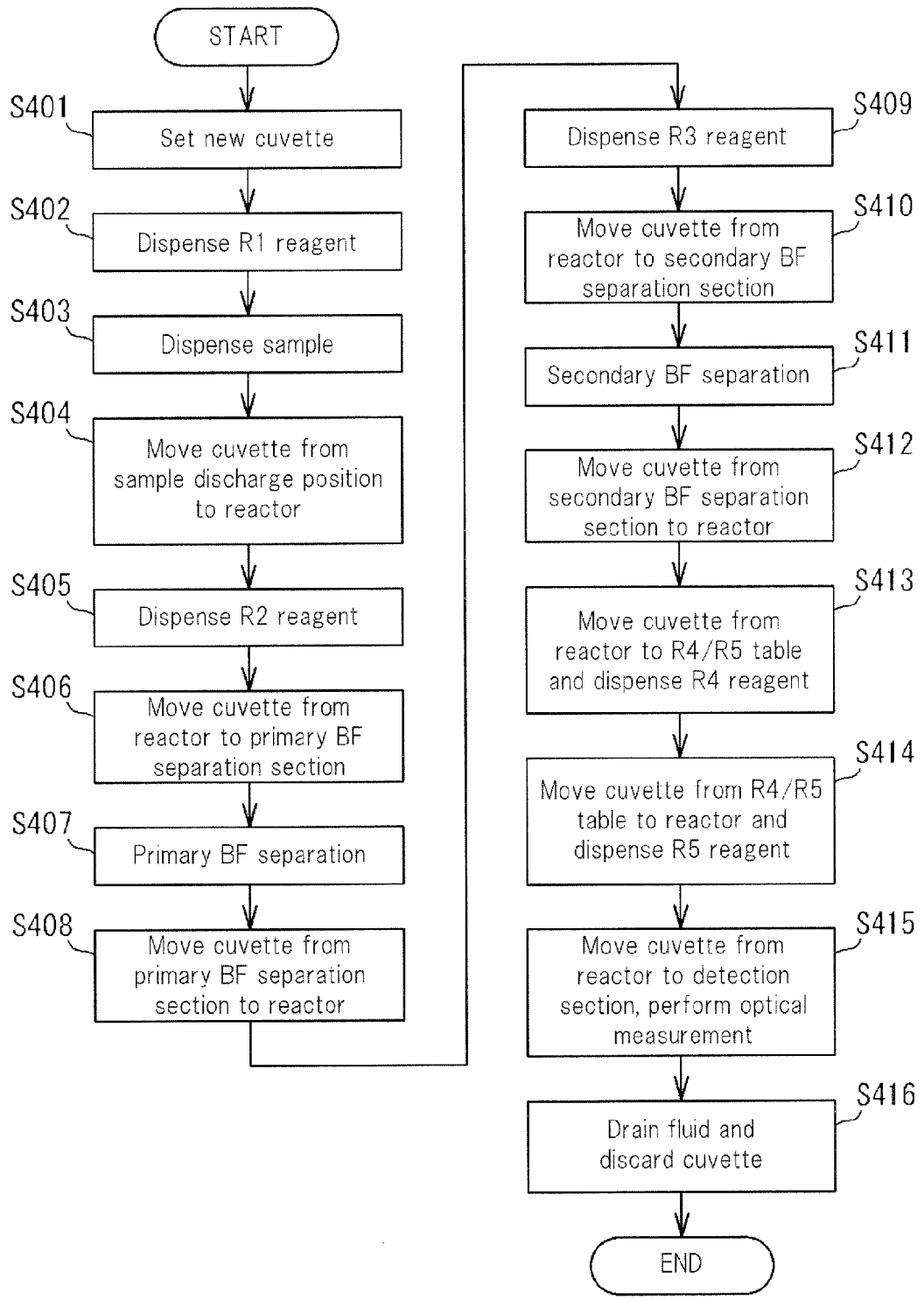
FIG. 4 is a flow chart of the sample measurement when the sample is not diluted.

Note that in the embodiment shown in FIG. 5 steps S501 through S506 replace steps S401 through S405 of FIG. 4, and following step S506 the same operations or processes are performed as in steps S404 through S416 of FIG. 4. Therefore, steps S501 through S506 specific to the embodiment of FIG. 5 are described below and the steps S404 through S416 duplicated in FIG. 4 are omitted for the sake of simplicity.

The controller 200 of the measurement section 2 first receives a measurement start signal from the main body 400 of the control device 4, and in step S501 the various drive mechanisms of the sample dispensing arm 5 and the like are placed on standby at the origin position, then the cuvette supplier 10 is actuated to deliver a new cuvette (dilution cuvette) to the discharging position 1b of the sample dispensing arm 5.

In step S502, the controller 200 of the measurement section 2 rotates the R1 reagent dispensing arm 6 until the tip of the pipette 6a of the R1 reagent dispensing arm 6 is positioned above the sample diluting fluid disposed on the reagent installation section 16, and aspirates a predetermined amount (for example, 195 µl) of diluting fluid using the pipette 6a. Thereafter, the R1 reagent dispensing arm 6 is rotated until the tip of the pipette 6a is positioned above the dilution cuvette arranged at the discharging position 1b, and the aspirated diluting fluid is dispensed into the cuvette.

In step S503, the controller 200 of the measurement section 2 aspirates the sample in the test tube that has been moved to the sample aspirating position 1a by the sample transport section 3 using the pipette tip mounted on the pipette end of the sample dispensing arm 5 at the tip installation position. Thereafter, the sample dispensing arm 5 is rotated until the pipette tip mounted on the pipette end of the sample dispensing arm 5 is positioned above the dilution cuvette disposed at the discharging position 1b, and a predetermined amount (for example 5 µl) of the aspirated sample is dispensed into the dilution cuvette. Thus, the sample is diluted $5/(195+5)=40$ times by the diluting fluid.

In step S504, the controller 200 of the measurement section 2 actuates the cuvette supplier 10 and sets a new cuvette (measurement cuvette) at the discharging position 1b of the sample dispensing arm 5. Note that the measurement cuvette and the dilution cuvette are same kind of cuvette and that both are supplied from the cuvette supplier 10. Although the used dilution cuvette is transported along the same pathway as the measurement cuvette, BF separation, reagent dispensing, and optical measurement processes are fully skipped, and ultimately the dilution cuvette is discarded in the disposal section 17 without optical measurement.

In step S505, the controller 200 of the measurement section 2 rotates the R1 reagent dispensing arm 6 until the tip of the pipette 6a of the R1 reagent dispensing arm 6 is positioned above the R1 reagent disposed on the reagent installation section 16, and aspirates a predetermined amount of R1 reagent using the pipette 6a. Thereafter, the R1 reagent dispensing arm 6 is rotated until the tip of the pipette 6a is positioned above the measurement cuvette arranged at the discharging position 1b, and the aspirated R1 reagent is dispensed into the measurement cuvette.

Then, in step S506, the controller 200 of the measurement section 2 aspirates the sample that has been diluted 40 fold within the dilution cuvette using the pipette tip mounted on the pipette end of the sample dispensing arm 5. Thereafter, the sample dispensing arm 5 is rotated until the pipette tip mounted on the pipette end of the sample dispensing arm 5 is positioned above the measurement cuvette disposed at the discharging position 1b, and a predetermined amount of the aspirated diluted sample is dispensed into the measurement cuvette.

After step S506, steps S404 through S416 are performed and the amount of light is measured by the detection section 14. The signal corresponding to the measured amount of light is transmitted to the controller 200, converted to a numerical value and stored in memory. The measurement value (numerical value) corresponds to the concentration of the antigen (component) contained in the dilution sample. This value is applied to the calibration curve prepared in a manner described later, to obtain the converted concentration.

[Calibration Curve Preparation and Correction Coefficient Calculation]

In the present embodiment, a calibration curve is prepared using a plurality of calibration samples containing known concentrations of measurement components prior to measuring the concentration of components in a measurement sample. A calibration curve is prepared for each measurement item. For example, a calibration curve is therefore prepared for the HBsAg measurement item using a plurality of calibration samples containing known concentrations of HBsAg, and a calibration curve is also prepared for the PIC measurement item using a plurality of calibration samples containing known concentrations of PIC. Correction coefficients are calculated to be used in the concentration calculation when a dilution sample is measured using the calibration curve. The calibration curve and the correction coefficient are stored in the ROM 202 of the controller 200.

Figure 10:
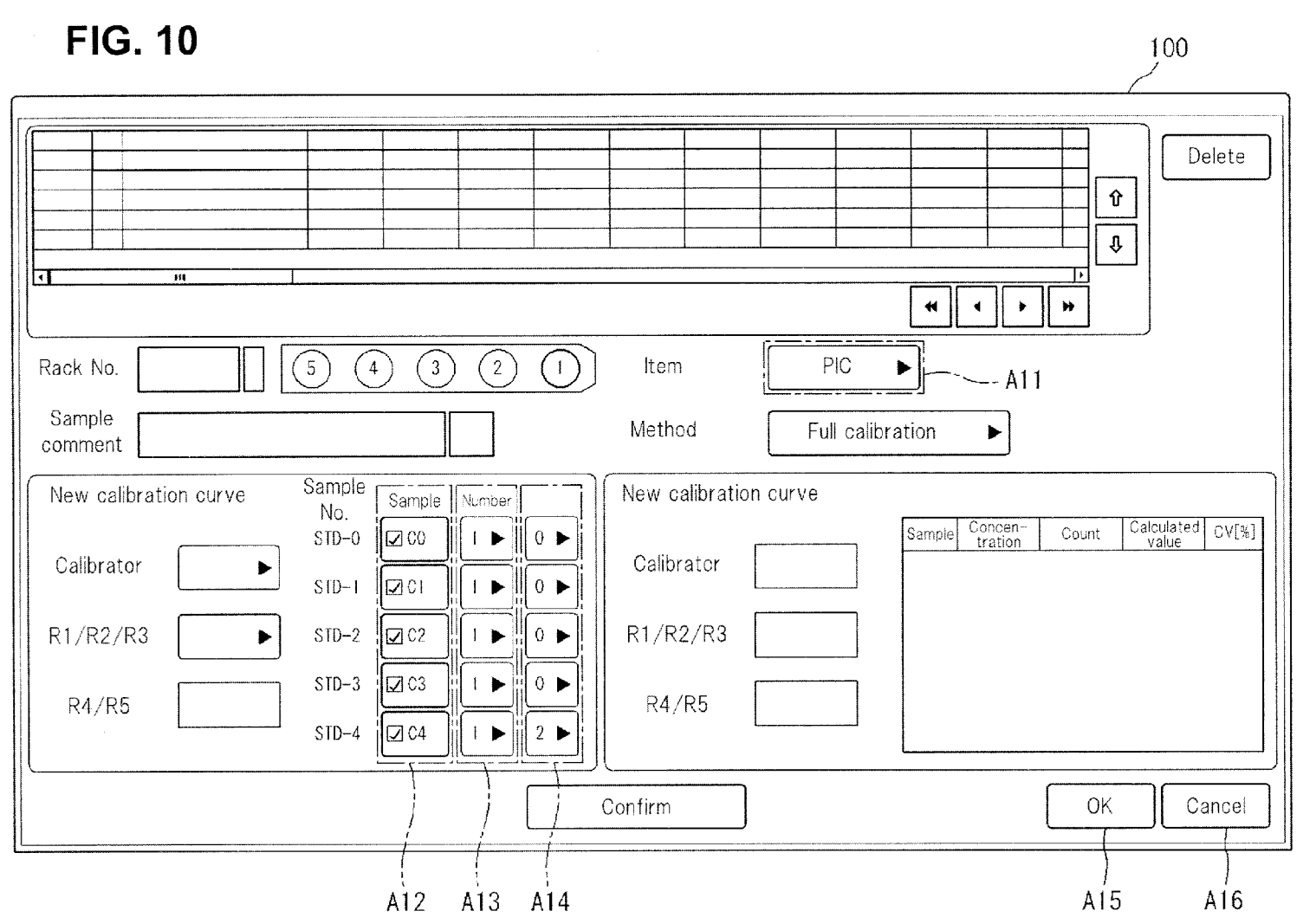

FIG. 10 shows an example of a calibration curve preparation request screen shown on the display input section 410. The calibration curve preparation request screen 100 includes an item selection column A11, calibrator selection column A12, number input column A13, diluting measurement number input column A14, OK button A15, and cancel button A16. The calibration curve preparation request screen 100 functions as an interface for receiving an instruction of a calibration curve preparation from the user to the immunoanalyzer 1, and also functions as an interface for receiving an instruction of a calibration sample diluting measurement from a user to the immunoanalyzer 1 when a number is entered in the diluting measurement number input column A14.

Figure 6:
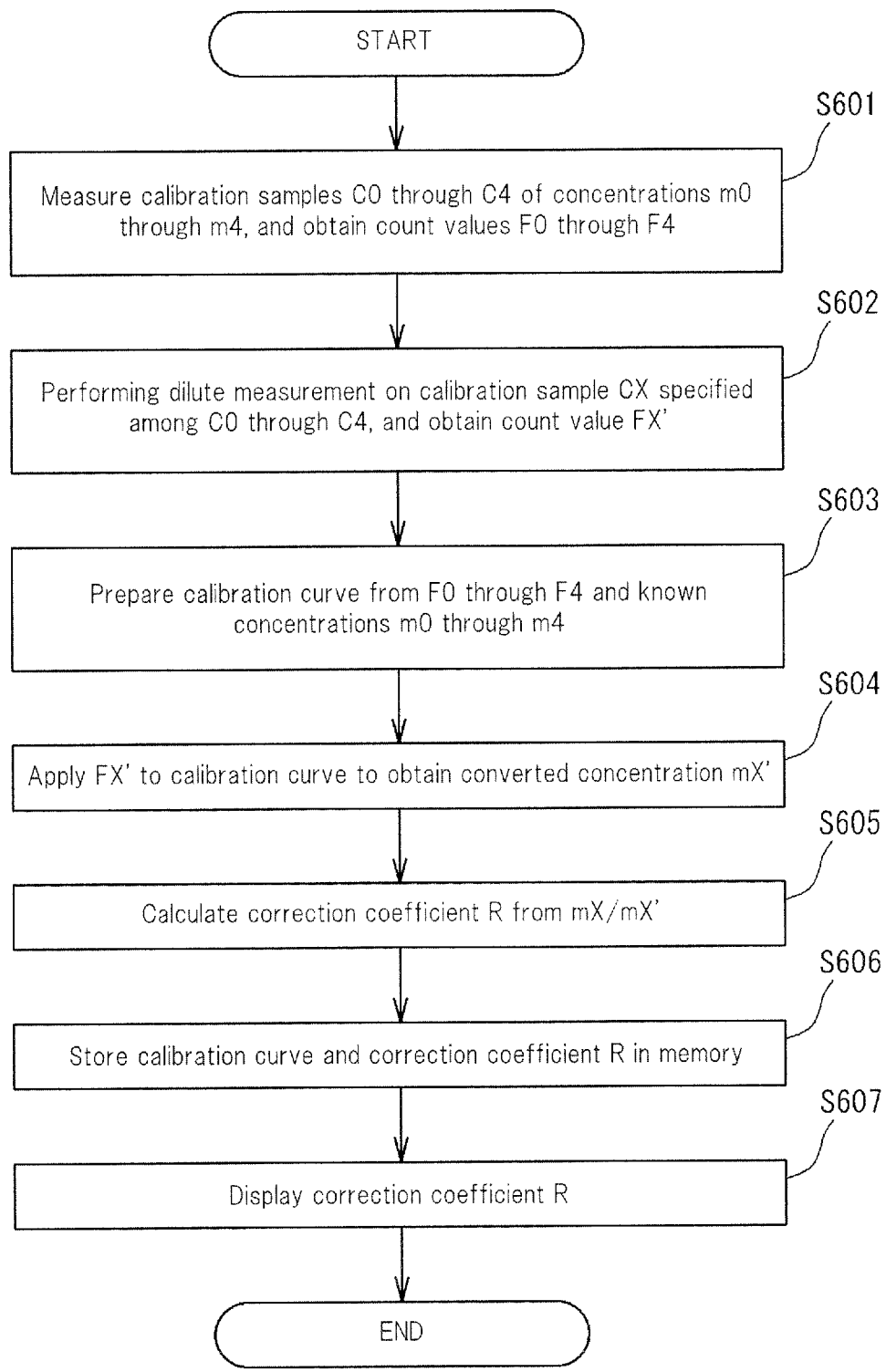
FIG. 6 shows the flows of the calibration curve preparation and the correction coefficient calculation.

FIG. 6 shows examples of the flows of the calibration curve preparation and the correction coefficient calculation. The user inputs whether to prepare a calibration curve of a desired measurement item (whether to perform calibration for any measurement item) from the item selection column A11 in the calibration curve preparation request screen 100 of FIG. 10. The item selection column A11 is a pull-down menu, and displays a plurality of measurement items in a pull down format by clicking the cursor on the column. The user specifies one measurement item from the list. In the example shown in FIG. 10, PIC is selected as the measurement item.

The user then selects the type of calibration sample to prepare the calibration curve from the calibrator selection column A12, and checks the check box corresponding to the desired calibration sample. In the example of FIG. 10, five calibration samples C0 through C4 including measurement component of known concentration are selected. Note that the concentration (hereinafter referred to as "indicated value") of the measurement component included in calibration samples C0 through C4 is m0 through m4, where $m0<m1<m2<m3<m4$. The number of calibration samples used when preparing a calibration curve is not limited to five, and may be four or less than four, or six or more than six. The indicated values of calibration samples C0 through C4 may be input beforehand by the user entering the value through the display input section 410 beforehand, or input beforehand by reading barcodes attached to the calibration samples C0 through C4 via a barcode reader that is not shown in the drawing, then storing the information in the controller 200 of the measurement section 2.

The user then inputs the number of measurements for calibration for each of the selected calibration samples C0 through C4 from the number input column A13. In the example of FIG. 10, a number is entered to measure each calibration sample one time.

The user then choices the calibration sample to be used for diluting measurements among the calibration samples C0 through C4, and determines the number of such measurements. The user enters this information from the diluting measurement number input column A14. In the example of FIG. 10, C4 is selected as the calibration sample to be used for diluting measurement, and two is entered as the number of diluting measurements.

When the above information is entered via the calibration curve preparation request screen 100 and the user selects the OK button A15, the input information is stored and calibration begins. When the cancel button A16 is selected, the entered information is deleted.

The user sets the calibration samples C0 through C4 in a sample rack and sets the sample rack in the sample transport section 3 before calibration. When the sample rack is set and the OK button A15 is selected on the calibration curve preparation request screen 100, the measurement section 2 start the measurement of the calibration sample according to the flow shown in FIG. 6.

In step S601, the controller 200 of the measurement section 2 sequentially measures the calibration samples C0 through C4 according to the previously described steps S401 through S415 (refer to FIG. 4), and obtains the measurement values (amount of light) F0 through F4. In the example of FIG. 10, each calibration sample is measured once since the measurement number of each calibration sample is [1]. Note that each calibration sample also may be measured several times (for example, three times) to improve the accuracy of the obtained calibration. In such case the measurement value of each calibration sample is the average value of several measurement values obtained by a plurality of measurements.

In step S602, the controller 200 of the measurement section 2 prepares a diluted calibration sample of user-specified calibration sample CX (X is selected from 0 through 4) which contains known concentration (referred as mX). The user-specified calibration sample CX is diluted 40 times. Measurements according to steps S501 through S506 and steps S404 through S415 (refer to FIG. 5) are performed, and the measurement value FX' is obtained and stored in memory. Since C4 is selected as the calibration sample to be used for diluting measurement in the example of FIG. 10, a diluted calibration sample is prepared by diluting C4 by 40 times and measurement is performed on it.

Although steps S601 and S602 are listed as separate steps in the drawing, in the actual measurement flow, step S602 is performed consecutively to the measurement of the calibration sample corresponding to step S601. For example, if the calibration sample C3 is specified for diluting measurement, the diluting measurement of C3 is performed following the undiluted measurement of C3 in step S601, and thereafter the measurement of C4 begins.

Figure 7:
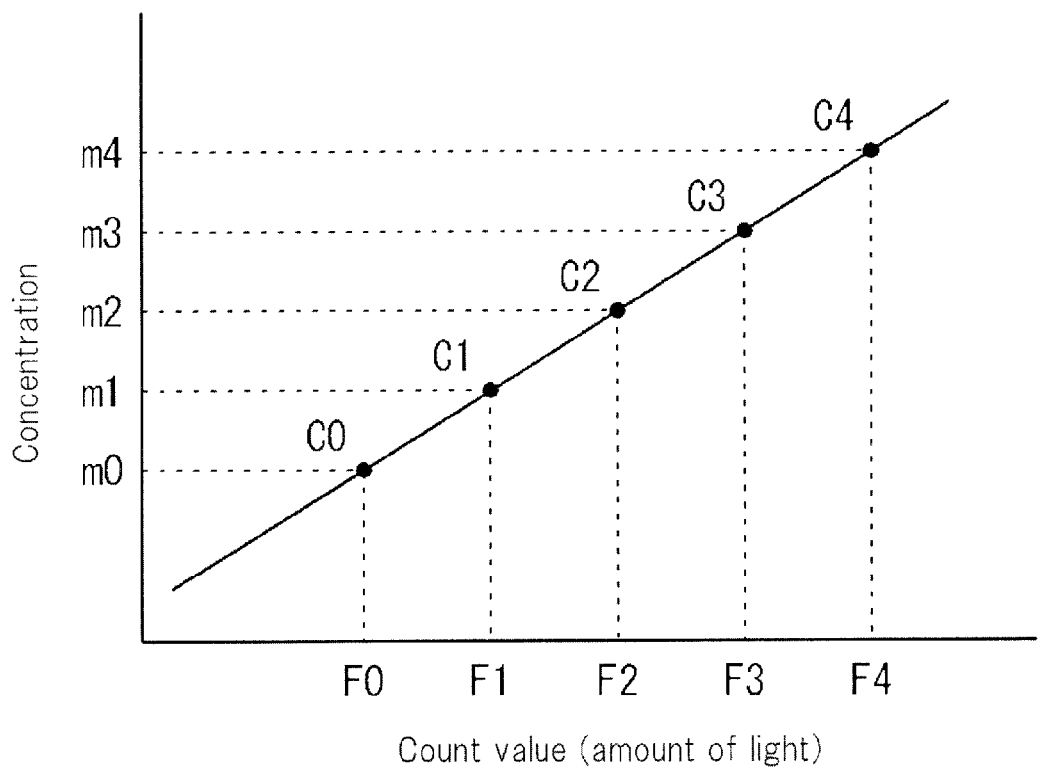
FIG. 7 shows an example of a calibration curve.

In step S603, the controller 200 of the measurement section 2 reads the stored indicated values m0 through m4 and prepares the calibration curve such as shown in FIG. 7 from the read indicated values m0 through m4 and the measurement values F0 through F4 obtained in step S601, then stores the prepared calibration curve together with the lot number of the calibration sample used to prepare the calibration curve in the ROM 202 of the controller 200. To facilitate understanding, in the example shown in FIG. 7, the intersections of the known concentration m and the measured value F are plotted on a straight line, however in an actual case, the plurality of intersections may not be linear. Therefore, approximate algorithms like as the least squares method or the like is used to determine the regressive line and regressive curve as the calibration curve.

In step S604, the controller 200 of the measurement section 2 applies the measurement value FX' measured in step S602 to the calibration curve prepared in step S603 to obtain the converted concentration mX'. When the diluting measurements of a calibration sample have been performed twice or more, the converted concentration mX' is calculated as the average value of the plurality of converted concentration values.

In step S605, the controller 200 of the measurement section 2 reads the indicated value mX stored in correspondence with the diluting measurement calibration sample CX, calculates the correction coefficient R=mX/mX' as the concentration ratio from the read indicated value mX and the converted concentration mX' obtained in step S604, and stores the calculated correction coefficient R and the prepared calibration curve in the ROM 202 of the controller 200 in step S606. The calculation of the correction coefficient R is illustrated by way of example pertaining to the obtained measurement values shown in Table 1.

In this example, the indicated value of the calibration sample C4 is 1.2, and since the average value of the converted concentration values of the diluted calibration sample C4 is 0.0314, the dilution correction coefficient R is 38.21 according to the following equation.

$$\text{Dilution correction coefficient } R = 1.2/0.0314 = 38.21.$$

Figure 11:
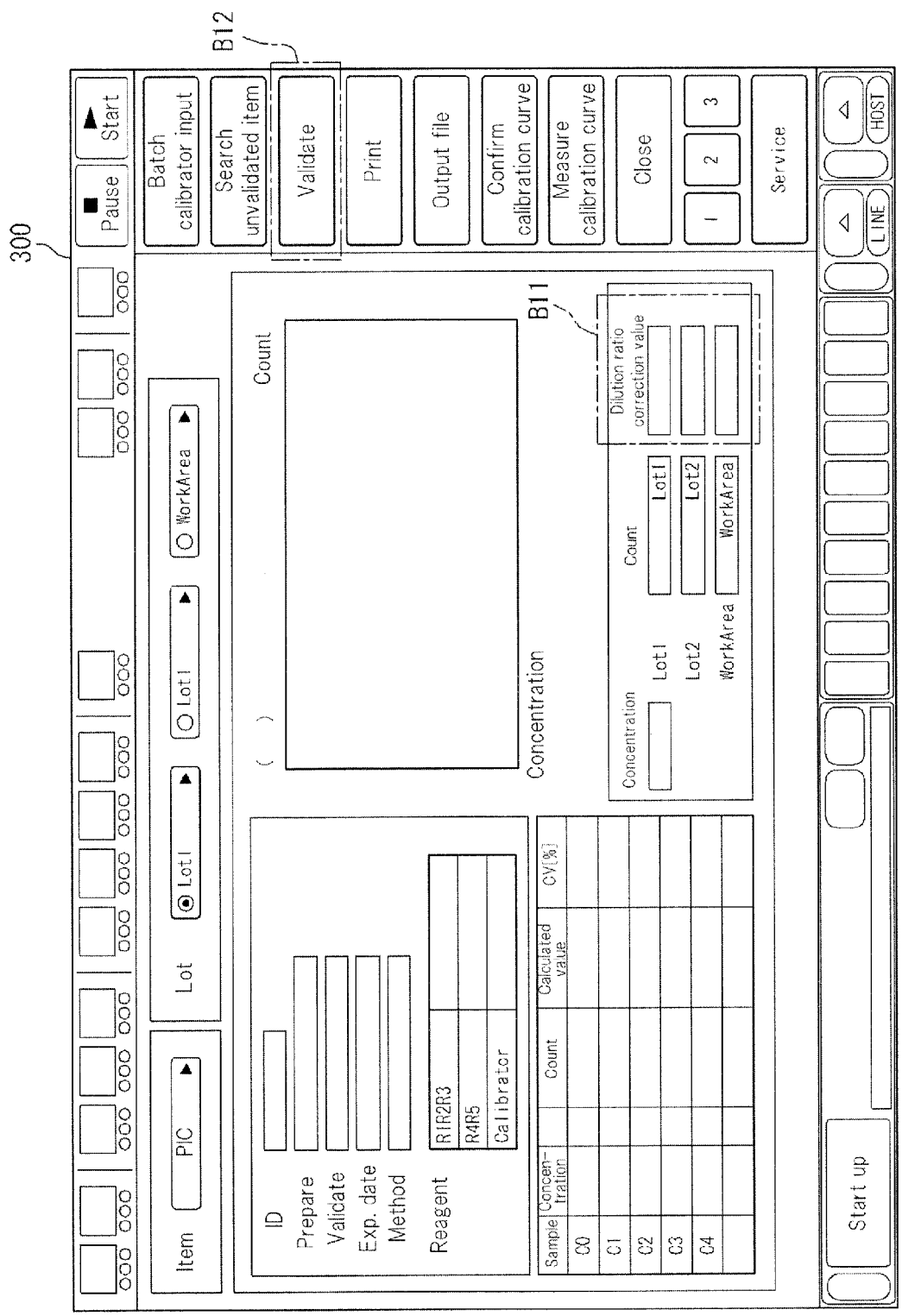
FIG. 11 shows an example of a calibration result screen.

In step S607, the display input section 410 displays a calibration result screen 300 to show the correction coefficient R. FIG. 11 shows a calibration result screen 300 that appears on the display input section 410. The calibration result screen 300 has a correction coefficient display column B11 where the correction coefficient R calculated in step S605 is displayed.

In the example of Table 1, the dilution correction coefficient R is 38.21 when the dilution ratio is set at 40 times, hence, in such case the error is 4.3% relative to expected value of 40. If the error from the dilution correction coefficient R displayed in the correction coefficient display column B11 is calculated and the error is within the acceptable range, the user selects the validate button B12 on the screen 300 to validate (approve) the calibration curve and the correction coefficient R.

On the other hand, when the dilution ratio is 40 times and the correction coefficient R is, for example, 30, there is an error of 25% relative to the expected value 40. In this case several causes should be considered, such as an error due to the quantifying accuracy of the pipette 5a of the sample dispensing arm 5 of the measurement section 2 or from the quantifying accuracy of the pipette 6a of the R1 reagent dispensing arm 6. Or there may be a problem in the diluting ability of the sample diluting fluid, hence, affinity of the sample diluting fluid and the reagent R1 may not be so good that the dilution linearity is lost. These factors can be mitigated by the user readjusting the dispensing mechanisms to increase the quantifying accuracy, or replacing the sample diluting fluid.

According to the above embodiment, the user can check whether the measurement section 2 is performing the desired dilution accurately by confirming whether the dilution correction coefficient R is within the desired range on the calibration result screen 300.

[Diluted Sample Measurement and Concentration Conversion]

Figure 8:
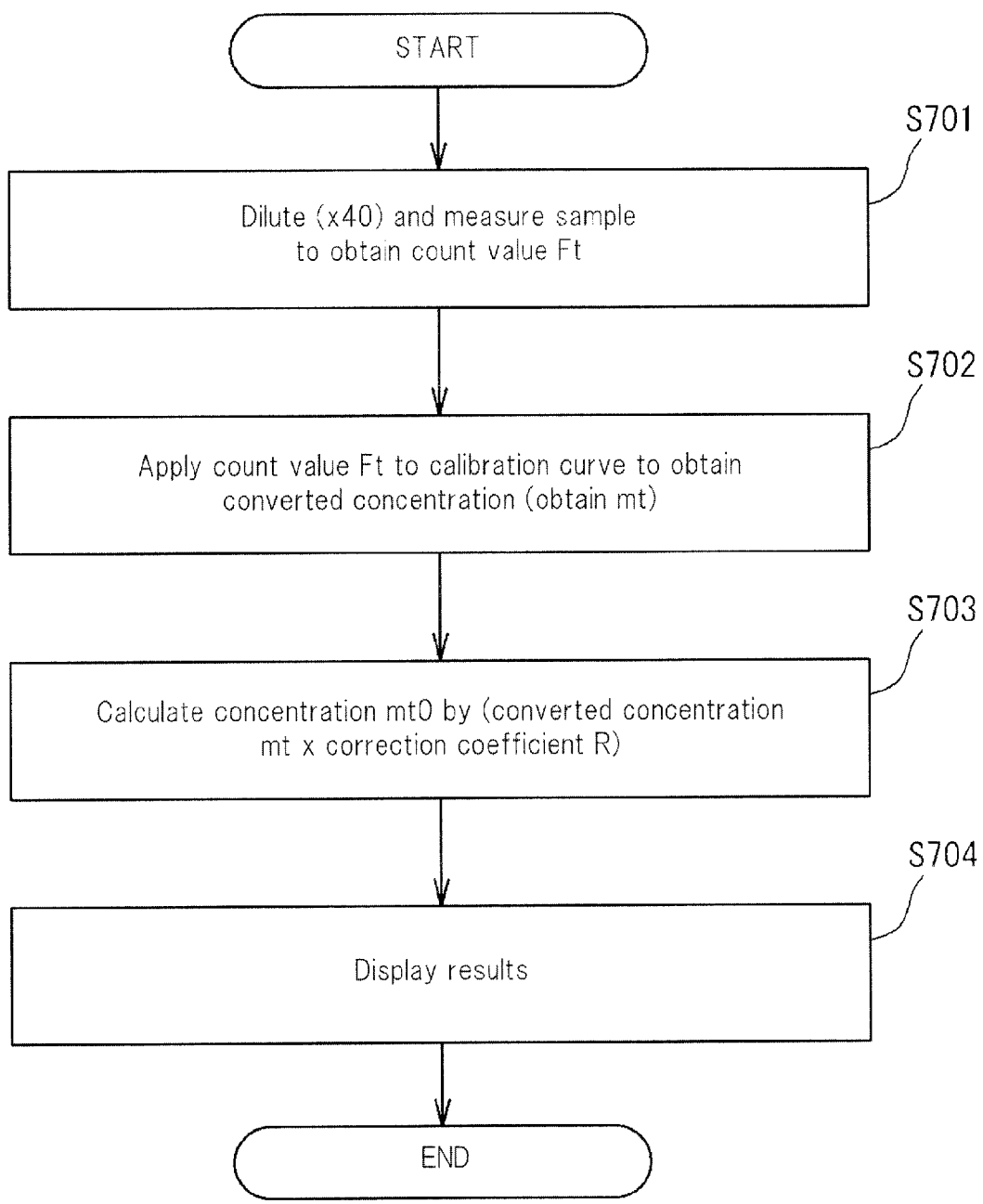
FIG. 8 shows the flow of the concentration conversion of a diluted sample.

Obtaining the concentration of a diluted sample using the calibration curve and correction coefficient determined according to the flow shown in FIG. 6 is described below referring to the flow chart of FIG. 8. Note that in the description of FIG. 8 the correction coefficient R is the correction coefficient determined at a dilution ratio of 40, and the dilution ratio of the sample is also 40.

First, in step S701, the controller 200 of the measurement section 2 dilutes a sample by 40 times to prepare a diluted sample according to steps S501 through S506 and performs a measurement on the diluted sample according to steps S404 through S415 to obtain the measurement value Ft.

TABLE 1

| Calibration sample | | C0 | C1 | C2 | C3 | C4 | Measurement value of diluting measurement for C4 | Converted concentration of diluted C4 |
|---|---|---|---|---|---|---|---|---|
| Indicated value | | 0 | 0.01 | 0.1 | 0.3 | 1.2 | | |
| Measurement value (count value) | First measurement | 523 | 47,921 | 496,882 | 1,499,902 | 5,537,675 | 143,763 | 0.0315 |
| | Second measurement | | | | | | 142,024 | 0.0313 |
| Average | | 523 | 47,921 | 496,882 | 1,499,902 | 5,537,675 | 142,894 | 0.0314 |

In step S702, the controller 200 of the measurement section 2 applies the measured value Ft obtained in step S701 to the calibration curve prepared in step S603 and stored in the ROM 202 of the controller 200 to acquire the converted concentration mt.

In step S703, the controller 200 of the measurement section 2 calculates the concentration mt0 by multiplying the converted concentration mt obtained in step S702 by the correction coefficient R calculated and stored in the ROM 202 of the controller 200 in step S605.

In step S704, the controller 200 of the measurement section 2 transmits the calculated concentration mt0 to the control device 4, and the main body 400 of the control device 4 shows the received result (concentration mt0) on the display input section 410. FIG. 9 shows a partial example of the display on the display input section 410. The result (concentration) of each measurement item is displayed in the measurement result column. When the sample has been diluted and measured, the dilution ratio is displayed in the dilution ratio column [1/40] shows that the sample was diluted by 40 times. And [1/1] shows that the sample was not diluted. When a diluting measurement has been performed, the dilution correction column shows whether a concentration calculation has been performed using the correction coefficient R or modified correction coefficient R' (described later). Mark is displayed when concentration calculation has been performed using the correction coefficient R or the modified correction coefficient R', and the column remains blank when concentration calculation has not been performed using the correction coefficient R or the modified correction coefficient R'. Whether the concentration calculation is performed using the correction coefficient R or the modified correction coefficient R' can be specified by the user for each measurement item in a screen (not shown in the drawings) used to specify the start of a sample measurement.

According to the above embodiment, the user can check whether the measurement section 2 is performing dilution with the desired dilution accuracy by the user confirming whether the dilution correction coefficient R is displayed on the calibration result screen 300 with the post dilution concentration and indicated value as comparative results, and that the dilution correction coefficient R is within the desired range. An accurate sample concentration can be determined by performing the diluting measurement of the sample and confirming the dilution accuracy.

Modifications

Note that the present invention is not limited to the above described embodiment and may be variously modified insofar as such modification are within the scope of the claims.

In the above embodiment, the dilution ratio (M1) of a sample to be measured and the dilution ration (M2) of the calibration sample used for determining the dilution correction coefficient R is same as 40 times. Even if the dilution ratios of M1 and M2 are different, the converted concentration mt0 of the sample may be calculate as shown below.

The concentration mt0 can be calculated by multiplying the converted concentration mt by the modified correction coefficient R' that derives from the correction coefficient R. The modified correction coefficient R' may be a coefficient obtained by, multiplying the dilution correction coefficient R by M1/M2. For example, when the calibration sample dilution ratio (M2) is 40 and the sample dilution ratio (M1) is 80, M1/M2 is 80/40=2. Then, the modified correction coefficient R' is obtained by doubling the correction coefficient R.

When the sample dilution ratio is M2×M2, the modified correction coefficient R' is obtained by squaring the correction coefficient R ($R^2$). For example, when the calibration sample dilution ratio is 40 and the sample dilution ratio is 1600, the square of the dilution correction coefficient R is used as the modified correction coefficient R'.

In the above embodiment the dilution accuracy is evaluated by the user comparing the diluting measurement ratio and the displayed dilution correction coefficient R when the dilution correction coefficient R is shown in the calibration result screen 300, however, the present invention is not limited to this method. For example, when the calibration sample C4 indicated value is 1.2 and the average value of the concentration conversion value is calculated as 0.0314 for the diluted calibration sample C4, these values may be displayed in comparable manner. Furthermore, the controller 200 may be configured to determine whether the ratio of these values exceeds a predetermined value (for example, the set dilution ratio), and displays the determination result.

Not only the dilution correction coefficient R, but also the dilution ratio can be displayed in calibration result screen 300. In a further modification, the dilution correction coefficient R is calculated and the error between the dilution correction coefficient R and the dilution ratio is calculated and displayed on the calibration result screen 300. In yet another modification, when the calculated error is outside a predetermined range, a warning is shown on the screen, and an audible sound is output to alert the user.

Although the correction coefficient is calculated using one calibration sample selected by the user from among the plurality of calibration samples used to prepare the calibration curves in the above embodiment, the correction coefficient also may be determined for two or more calibration samples. For example, when the dilution measurements are performed on the calibration samples C1 through C3, the correction coefficients R1, R2, and R3 are determined as [32], [35], and [34] respectively. And the dilution ratio is 40. In this case, [33.7] is calculated as the average value of [32], [35], and [34]. This value is set as the correction coefficient R for diluting measurements where the dilution ratio is 40. In another case, for example, a sample is diluted and measured, and the converted concentration value is between the known concentration m1 of the calibration sample C1 and the known concentration m2 of the calibration sample C2 when the measurement value is applied to the calibration curve. In this case, the average value of the correction coefficient of the calibration sample C1 [32] and the correction coefficient of the calibration sample C2 [35] is 33.5 and this value is set as the correction value. Or the correction coefficient [32] is used when the converted concentration value is near m1, whereas the correction coefficient [35] is used when the converted concentration value is near m2.

Although the correction coefficient is determined using one calibration sample selected among the calibration samples C1 through C4 used to prepare the calibration curve in the above embodiment, the present invention is not limited to this arrangement inasmuch as the correction coefficient also may be determined using a special calibration sample C5 for determining a correction coefficient.

Although the correction coefficient obtained from measuring the diluted calibration sample is stored in the memory section ROM 202 in the above embodiment, the correction coefficient not always have to be determined and stored in the memory. The concentrations of components contained in the sample can be calculated on the basis of a first concentration of a diluted sample and a known concentration of a calibration sample, and a second concentration of a diluted calibration sample. That is, when the dilution ratio of the sample is designated M1 and the dilution ratio of the calibration sample is designated M2, the concentration of the component contained in the sample can be calculated as [the first concentration]×(known concentration of calibration sample/second concentration)×(M1/M2).

Although the above embodiment is described only in terms of using the predetermined correction coefficient R to determine the concentration of a sample, a mode for calculating the dilution ratio by multiplication using a conventional method where the dilution ratio is used on behalf of the correction coefficient, and a mode for calculating using a correction coefficient may be selectable. In this case, which mode was used to calculate the concentration is preferably displayed in an identifiable manner on the measurement result display screen as in FIG. 9.

Although the above embodiment pertains to an immunoanalyzer that examines various items such as hepatitis type B, hepatitis type C, tumor marker, and thyroid hormone using a sample such a blood as an example of a sample analyzer, the present invention is not limited to this example inasmuch as the invention is applicable diluting measurement of samples in apparatuses for measuring the concentrations of components in the sample using a calibration curve.

What is claimed is:

1. A sample analyzer comprising:
    a measurement section configured to perform a measurement on a sample to quantify an analyte in the sample; and
    a computer;
    wherein the computer is programmed to perform a calibration operation (A), and a sample analysis operation (B),
    the calibration operation (A) comprising:
        (A-1) causing the measurement section to perform a measurement on a plurality of calibration samples, each containing an analyte of known concentration;
        (A-2) causing the measurement section to dilute a calibration sample containing an analyte of known concentration X at a predetermined dilution ratio with a diluting fluid and to perform a measurement on the diluted calibration sample;
        (A-3) preparing a calibration curve based on the known concentrations of the calibration samples and the measurement results of (A-1); and
        (A-4) applying the measurement result of (A-2) to the prepared calibration curve to determine a converted concentration X0,
    the sample analysis operation (B) comprising:
        (B-1) causing the measurement section to dilute a sample to be measured at a predetermined sample dilution ratio with a diluting fluid and to perform a measurement on the diluted sample;
        (B-2) applying the measurement result of (B-1) to the calibration curve prepared to determine a concentration Y0; and
        (B-3) using the concentration Y0 and a correction coefficient comprising a concentration ratio of the known concentration X and the converted concentration X0 to determine the sample concentration Y.

2. The sample analyzer of claim 1, wherein (A) the calibration operation comprises: displaying on a display of the computer a screen for selecting a calibration sample to be measured in (A-2) among the plurality of calibration samples.

3. The sample analyzer of claim 2, wherein the screen comprises a menu specifying the number of measurements of the calibration sample in (A-2), and the computer performs the number of measurement in (A-2) specified by the menu and determines the concentration X0 in (A-4) based on the average value of the measurement results of the measurements of (A-2).

4. The sample analyzer of claim 1, wherein when preparing the calibration curve, the measurement section performs a plurality of measurements of each of the plurality of calibration samples; and
    the computer is programmed to determine for each of the plurality of calibration samples an average value of a plurality of measurement values obtained by performing the plurality of measurements on each respective calibration sample as a representative measurement value, and prepares the calibration curve based on the representative measurement value and the known concentration of the respective calibration sample.

5. The sample analyzer of claim 1, wherein the computer includes a display unit, and the display unit shows the concentration of the analyte in the sample determined using the correction coefficient together with information indicating that the concentration was determined based on the correction coefficient.

6. The sample analyzer of claim 1, wherein the measurement section quantifies the analyte by optically measuring the analyte in the sample.

7. The sample analyzer of claim 1, wherein the computer includes a display unit, and the display unit shows a screen including the correction coefficient and the predetermined sample dilution ratio.

8. The sample analyzer of claim 1, wherein the computer outputs a warning when a relationship between the concentration ratio and the predetermined dilution ratio does not satisfy a predetermined condition.

9. The sample analyzer of claim 1, further comprising a transport section configured to transport a rack capable of holding a plurality of containers containing sample, wherein when a plurality of containers containing the plurality of calibration samples are placed in the rack and the rack is transported to the measurement section by the transport section, the measurement section consecutively performs measurement of the calibration samples to prepare the calibration curve, and performs a measurement of at least one of the diluted calibration samples.

10. The sample analyzer of claim 1, wherein the sample is a serum sample.

11. The sample analyzer of claim 1 further comprising:
    a reagent installation section for accommodating a reagent that causes an antigen-antibody reaction between the analyte and the reagent; and
    a reagent dispensing arm configured to dispense the reagent in the reagent installation section.

12. The sample analyzer of claim 11, wherein the analyte is an antigen; and the reagent includes an antibody which is capable of binding to the antigen.

13. The sample analyzer of claim 12, wherein the antibody is a labeling antibody.

14. The sample analyzer of claim 13, wherein the reagent installation section is capable of accommodating a luminescent substrate which luminesces by a reaction with the labeling antibody.

15. A sample analyzer comprising:
    a measurement section configured to perform a measurement on a sample to quantify an analyte in the sample; and
    a computer;

wherein the computer is programmed to perform (A) a calibration operation, and (B) a sample analysis operation, (A) the calibration operation comprising:

(A-1) causing the measurement section to perform a measurement on a plurality of calibration samples, each containing an analyte of known concentration;

(A-2) causing the measurement section to dilute a calibration sample containing an analyte of known concentration X at a predetermined ratio with a diluting fluid and to perform a measurement on the diluted calibration sample;

(A-3) preparing a calibration curve based on the known concentrations of the calibration samples and the measurement results of (A-1); and (A-4) applying the measurement result of (A-2) to the prepared calibration curve to determine a converted concentration X0, (B) the sample analysis operation comprising:

(B-1) causing the measurement section to dilute a sample to be measured at a predetermined ratio with a diluting fluid and to perform a measurement on the diluted sample;

(B-2) applying the measurement result of (B-1) to the calibration curve prepared to determine a concentration Y0; and (B-3) using the concentration Y0 and a correction coefficient comprising the ratio of the known concentration X and the converted concentration X0 to determine the sample concentration Y, wherein the measurement section quantifies the analyte by optically measuring the analyte in the sample, wherein the sample analyzer, further comprises:

a reagent installation section for accommodating a reagent that causes an antigen-antibody reaction between the analyte and the reagent; and a reagent dispensing arm configured to dispense the reagent set in the reagent installation section.

16. The sample analyzer of claim 15, wherein the analyte is an antigen; and the reagent includes an antibody which is capable of binding to the antigen.

17. The sample analyzer of claim 16, wherein the antibody is a labeling antibody.

18. The sample analyzer of claim 17, wherein the reagent installation section is capable of accommodating a luminescent substrate which luminesces by a reaction with the labeling antibody.

19. The sample analyzer of claim 15, wherein the sample is a serum sample.

20. A sample analyzer comprising:

a measurement section configured to perform a measurement on a sample to quantify an analyte in the sample, wherein the sample is a serum sample;

a reagent installation section for accommodating a reagent that causes an antigen-antibody reaction between the analyte and the reagent;

a reagent dispensing arm configured to dispense the reagent set in the reagent installation section; and a computer;

wherein the computer is programmed to perform (A) a calibration operation, and (B) a sample analysis operation, (A) the calibration operation comprising:

(A-1) causing the measurement section to perform a measurement on a plurality of calibration samples, each containing an analyte of known concentration;

(A-2) causing the measurement section to dilute a calibration sample containing an analyte of known concentration X at a predetermined ratio with a diluting fluid and to perform a measurement on the diluted calibration sample;

(A-3) preparing a calibration curve based on the known concentrations of the calibration samples and the measurement results of (A-1); and (A-4) applying the measurement result of (A-2) to the prepared calibration curve to determine a converted concentration X0, (B) the sample analysis operation comprising:

(B-1) causing the measurement section to dilute a sample to be measured at a predetermined ratio with a diluting fluid and to perform a measurement on the diluted sample;

(B-2) applying the measurement result of (B-1) to the calibration curve prepared to determine a concentration Y0; and (B-3) using the concentration Y0 and the ratio of the known concentration X and the converted concentration X0 to determine the sample concentration Y.

* * * * *